(12) United States Patent
Qin et al.

(10) Patent No.: US 7,727,152 B2
(45) Date of Patent: Jun. 1, 2010

(54) METHOD AND APPARATUS FOR SCANNING CONFOCAL ACOUSTIC DIAGNOSTIC FOR BONE QUALITY

(75) Inventors: Yixian Qin, Port Jefferson Station, NY (US); Clinton Rubin, Port Jefferson, NY (US); Wei Lin, Port Jefferson, NY (US)

(73) Assignee: The Research Foundation of State University of New York, Albany, NY (US)

( * ) Notice: Subject to any disclaimer, the term of this patent is extended or adjusted under 35 U.S.C. 154(b) by 1267 days.

(21) Appl. No.: 10/522,452

(22) PCT Filed: Feb. 28, 2002

(86) PCT No.: PCT/US02/06141

§ 371 (c)(1),
(2), (4) Date: Jun. 9, 2005

(87) PCT Pub. No.: WO02/071949

PCT Pub. Date: Sep. 19, 2002

(65) Prior Publication Data

US 2005/0283072 A1    Dec. 22, 2005

Related U.S. Application Data

(60) Provisional application No. 60/271,957, filed on Feb. 28, 2001.

(51) Int. Cl.
*A61B 8/00* (2006.01)
*G01H 15/00* (2006.01)

(52) U.S. Cl. ............................ 600/449; 73/599; 73/597; 600/438

(58) Field of Classification Search ................. 600/442, 600/438, 449; 73/597, 599
See application file for complete search history.

(56) References Cited

U.S. PATENT DOCUMENTS

4,774,959 A    10/1988    Palmer et al.

(Continued)

FOREIGN PATENT DOCUMENTS

| EP | 299906 A2 * | 1/1989 | .................. 600/443 |
| GB | 2065303 A * | 6/1981 | .................. 600/449 |

OTHER PUBLICATIONS

Fatemi, M.; Greenleaf, J.F., "Coherent ultrasound stimulated acoustic emission imaging," Ultrasonics Symposium, 1997. Proceedings., 1997 IEEE , vol. 2, no., pp. 1411-1414 vol. 2, Oct. 5-8, 1997.*

(Continued)

*Primary Examiner*—Eric F Winakur
*Assistant Examiner*—Helene Bor
(74) *Attorney, Agent, or Firm*—The Farrell Law Firm, LLP (57) ABSTRACT

The invention comprises a system and method for determining at least one material property of a material sample (such as a bone sample) at at least one point. The system includes a transmitting ultrasonic transducer and a receiving ultrasonic transducer, both transducers being confocal transducers. The transducers are configured to receive the material sample therebetween such that the confocal point of the transducers are located at the at least one point in the material sample. A processor initiates an ultrasonic signal from the transmitting transducers that is transmitted trough the at least one point of the material sample when positioned between the transducers. The ultrasonic signal is received by the receiving transducing and the processor in turn receives a signal reflecting one or more measures of the received ultrasonic signal. The processor determines at least one ultrasonic parameter for the at least one point of the material sample based upon the transmitted and received ultrasonic signals. The processor further determines the at least one material property at the point of the sample based upon the at least one ultrasonic parameter.

27 Claims, 4 Drawing Sheets

U.S. PATENT DOCUMENTS

| | | | |
|---|---|---|---|
| RE32,782 E * | 11/1988 | Pratt, Jr. | 600/442 |
| 4,913,157 A | 4/1990 | Pratt, Jr. et al. | |
| 4,976,267 A | 12/1990 | Jeffcott et al. | |
| 5,119,820 A | 6/1992 | Rossman et al. | |
| 5,143,069 A | 9/1992 | Kwon et al. | |
| 5,197,475 A | 3/1993 | Antich et al. | |
| 5,218,963 A | 6/1993 | Mazess | |
| 5,348,009 A | 9/1994 | Ohtomo et al. | |
| 5,433,203 A | 7/1995 | Kimura et al. | |
| 5,564,423 A | 10/1996 | Mele et al. | |
| 5,603,325 A | 2/1997 | Mazess et al. | |
| 5,615,681 A | 4/1997 | Ohtomo | |
| 5,704,360 A | 1/1998 | Coulter | |
| 5,785,656 A * | 7/1998 | Chiabrera et al. | 600/449 |
| 5,806,520 A | 9/1998 | Berger et al. | |
| 5,807,250 A | 9/1998 | Ohtomo et al. | |
| 5,817,018 A | 10/1998 | Ohtomo | |
| 5,840,029 A * | 11/1998 | Mazess et al. | 600/437 |
| 5,879,301 A | 3/1999 | Chiabrera et al. | |
| 5,921,929 A | 7/1999 | Goll et al. | |
| 6,027,449 A | 2/2000 | Wiener et al. | |
| 6,029,078 A | 2/2000 | Weinstein et al. | |
| 6,086,538 A | 7/2000 | Jorgensen et al. | |
| 6,095,979 A * | 8/2000 | Ohtomo | 600/449 |
| 6,221,019 B1 * | 4/2001 | Kantorovich | 600/449 |
| 6,328,695 B1 * | 12/2001 | Vammen et al. | 600/442 |
| 6,468,215 B1 * | 10/2002 | Sarvazyan et al. | 600/438 |
| 6,740,041 B2 * | 5/2004 | Faulkner et al. | 600/449 |
| 6,875,176 B2 * | 4/2005 | Mourad et al. | 600/442 |
| 6,899,680 B2 * | 5/2005 | Hoff et al. | 600/449 |
| 7,112,173 B1 * | 9/2006 | Kantorovich et al. | 600/449 |

OTHER PUBLICATIONS

Laugier, P.; Giat, P.; Droin, P.; Saied, A.; Berger, G., "Ultrasound images of the os calcis: a new method of assessment of bone status," Ultrasonics Symposium, 1993. Proceedings., IEEE 1993, vol., no., pp. 989-992 vol. 2, Oct. 31-Nov. 3, 1993.*

P. Laugier et al.; "Ultrasound Images of the OS Calcis: A New Method of Assessment of Bone Status"; Oct. 1993; pp. 989-992.

P. Laugier et al.; "Ultrasound Parametric Imaging of Bone in Vivo"; Nov. 1995; pp. 1137-1140.

Peyman Hadji, MD,[1] et al.; "Quantitative Ultrasound of OS Calcis in Postmenopausal Women With Spine and Hip Fractures"; pp. 233-239.

* cited by examiner

METHOD AND APPARATUS FOR SCANNING CONFOCAL ACOUSTIC DIAGNOSTIC FOR BONE QUALITY

CROSS-REFERENCE TO RELATED APPLICATION

This application claims priority to U.S. Provisional Application 60/271,957, filed Feb. 28, 2001 entitled "Scanning confocal acoustic diagnostic method and apparatus for bone assessment". The contents of the aforesaid U.S. Provisional Application 60/271,957 are hereby incorporated by reference.

GOVERNMENT RIGHTS

This invention was made with Government support under Grant No. TD00207 awarded by the National Space Biomedical Research Institute. The U.S. Government has certain rights in the invention.

BACKGROUND OF THE INVENTION

1. Field of the Invention

This invention deals generally with diagnostic methods and apparatus for determining the condition and quality of bones and other materials. In particular, it discloses a method for determining non-invasively, non-destructively, ex vivo or in vivo, the condition and quality of certain bones in humans and animals.

2. Description of the Related Art

The need for assessing the mechanical properties of a material is found in a wide variety of applications. For example, it is necessary to test the strength of materials in a wide variety of industrial applications non-invasively and non-destructively. In many applications, destructive testing techniques can be utilized to determine the mechanical properties of a material. In other types of material testing, the material is easily accessible for analysis and nondestructive techniques can be utilized. Further, many materials are homogenous on a macroscopic level, permitting simplified techniques based upon assumptions of the homogeneity.

While many different techniques have been developed for investigating the mechanical properties of materials, many types of materials are not accurately analyzed using conventional techniques. For example, in many medical applications, it is desirable to determine the mechanical properties of the material for proper diagnosis and treatment. In many medical applications, however, the testing is difficult to analyze because destructive testing cannot be used, invasive types of testing are undesirable, and the non-homogenous nature of biological tissue presents unique problems. A good example is the need for accurate measurement of bone mass and bone strength as an indication of resistance to fracture and a condition for bone quality.

The capability to accurately assess resistance to fracture and the status of bone quality has great clinical significance in the diagnosis and treatment of numerous medical problems such as osteoporosis. Osteoporosis affects one in three women and one in five men over the age of 60. Over 80% of the one million fractures sustained yearly by women over the age of 50 in the United States is a consequence of osteoporosis. Half of the patients with fractures resulting from osteoporosis never recover normal functions, and 30% progress to premature death, 10% dying within three months because of peri- and post-operative complications. However, treatments exist which alter, delay or reverse the progression of osteoporosis if the disease is accurately diagnosed before fracture occurs or if the risk of fracture can be assessed. The development of improved treatments would be greatly facilitated by a technique capable of delineating their effectiveness.

In osteoporosis, bone mass is lost gradually and progressively thus altering the macro and micro bone structure and decreasing the mechanical strength of the skeleton until bone fracture due to minimal trauma results. Bones are composed of cortex (compact bone) and trabeculae (sponge bone). From the tissue level regions of bone that experience relatively high stiffness tend more towards cortical bone. Regions of bone experiencing low stiffness tend to be more trabecular. In most sites of trabecular bone, the trabecular mass is surrounded by a relatively thin layer of cortical bone which may vary in thickness between individuals. Osteoporosis is manifest as an absolute decrease in bone tissue mass primarily in the trabecular region. A person suffering from osteoporosis loses initially a greater proportional amount of trabecular bone than cortical bone.

3. Description of Current Methods

The prior art includes various approaches to measurements related to bone characteristics:

U.S. Pat. No. 4,774,959 (Palmer) purports to describe an apparatus in which a bone containing body member to be tested is placed between a pair of transducers and a predetermined sequence of tone signals having frequencies spanning a range from 200 to 600 kHz is transmitted through the body member. Amplitudes of the received signals are used to calculate the rate of change of attenuation of ultrasound transmission of the body member with respect to frequency. The rate of change of attenuation is used along with a bone width measurement in a calculation that purports to correlate reliably with changes in bone characteristics which occur with the onset of osteoporosis. Palmer does not describe the purported correlation or its reliability in any detail. Among other problems with Palmer, each single ultrasonic measurement covers a large portion of bone, such as a patient's heel. In any case, the frequencies used in Palmer would not be able to provide for measurement of a relatively small region of bone.

U.S. Pat. No. 4,913,157 (Pratt) describes similar apparatus as Palmer. Again, each single ultrasonic measurement covers a large portion of bone, such as the kneecap. From the data measured by passing ultrasound through the bone, certain ultrasound characteristics are derived, such as velocity of the ultrasound in the bone. The bone velocity of a patient is compared with a database of bone velocities, age and corresponding bone density conditions for a group of patients. Pratt purports to determine the patent's relative bone condition by comparing the bone velocity of the patient as measured to the spectrum of velocities for the patient's age. Among other deficiencies, Pratt does not describe this empirical correlation or its reliability in any detail.

U.S. Pat. No. 5,119,820 (Rossman) discloses apparatus for use in ultrasound bone density measurements in which a pair of ultrasound transducers are mounted on the arms of a caliper so that they may be placed on either side of the bone under test. From the data measured by passing ultrasound through the bone, certain ultrasound characteristics are derived, such as broadband ultrasonic attenuation. Physical properties and integrity are purportedly determined by comparing the ultrasound characteristics with a material of known acoustic properties. Alternatively, comparison may be made with a database of patients, similar to the Pratt patent.

U.S. Pat. No. 5,921,929 (Goll, et. al) discloses apparatus for use in ultrasound bone density measurements. The apparatus measures or calculates a number of "Ultrasonic Bone Indices" ("UBI") from emitted and received ultrasound for a number of bone locations. Regions of interest in the bone are identified, for example, a region surrounding a minimum with respect to a particular UBI parameter. Certain UBIs are said by Goll to be measures of bone properties; for example, the UBI corresponding to an autoregressive moving average spectral estimation function of the stored output of the transducer is purported to be usable as a measure of bone porosity and non-connectivity.

U.S. Pat. No. 6,086,538 (Jorgensen, et al.) similarly discloses emitting and receiving ultrasonic transducers for taking ultrasonic measurements at a number of locations of a patient's bone. Various ultrasonic properties are measured or calculated, such as speed of sound transmission in the bone (SOS) or broadband ultrasonic attenuation (BUA). The ultrasonic data is said to be used to define the location of select internal anatomical features of the bone. The attenuation measures are said to be used to display an image. Jorgensen also makes a brief reference to comparing BUA and SOS values for a patient with ranges of such values for a large number of patients, similar to the database concept of Pratt and Rossman. Jorgensen does not describe this purported empirical correlation or its reliability in any detail.

SUMMARY OF THE INVENTION

It would be desirable to use ultrasound to measure small regions of the bone, such as at the trabeculae region or level, which is on the order of approximately 0.5 mm. Variations of ultrasonic measurements and parameters at this level are highly correlated to bone properties, such as bone mineral density (BMD) and Stiffness. One way of using ultrasound to increase the resolution and measure smaller properties is to use higher frequency ultrasound. However, as the frequency of the ultrasound is increased, the energy of the ultrasonic wave attenuates more rapidly in the material. This is especially problematic in using ultrasound on a bone in a live person, where the ultrasonic wave must pass through a large amount of tissue, bone, etc. Thus, it would be desirable to utilize higher frequency ultrasound to measure smaller bone properties while adjusting the energy of the ultrasonic wave accordingly.

It would also be desirable to provide a rigorous correlation between ultrasonic measurements and parameters relating to a bone and bone properties, such as BMD and Stiffness. It would also be desirable to provide such a rigorous correlation over a small area of the bone, such as at the trabeculae level, where variations in the ultrasonic parameters are highly correlated to such bone properties. It would also be desirable to perform such measurements at determinations of bone properties at highly refined and resolvable increments over a two or three dimensional region of the bone, for further imaging and rigorous analysis of patterns in the bone properties at the trabeculae level, for example, using fractal analysis.

This invention pertains to detecting bone disease and other abnormal bone conditions, as well as evaluating bone quality, among other things. A principle object is to diagnose the presence of osteoporosis. However, other conditions may also be detected using this method, including bone conditional variations following renal failure and periodontal disease due to bone deterioration. The invention may also be useful both for detecting fractures and for assessing, quantitatively, the healing of fractures.

The present invention disclosed herein improves significantly on the prior art and is useful in determining the following tissue characteristics: bone density, bone strength, bone architecture, bone quality and fracture risk as well as other characteristics of bone tissue and other tissues. The present invention is particularly advantageous over current techniques in that it can determine bone properties at the trabeculae region, which is a much smaller level than bulk trabecula strength, using ultrasound parameters.

The present invention comprises apparatus that uses ultrasound on the bone of a living patient, where the ultrasound is of a relatively large frequency that is capable of providing ultrasonic measurements and parameters for the bone at the trabeculae level. Focusing of the acoustic signal using confocal transducers in the present invention compensates for the rapid attenuation of energy in the material due to the increased frequency.

In addition, the present invention calculates a determination of bone properties, such as BMD and Stiffness, from the ultrasonic measurements and parameters. The invention provides a rigorous correlation between the ultrasonic measurements and parameters and bone properties. For example, the present invention applies regression analysis of ultrasonic measurements and parameters (such as ultrasonic velocity and ultrasonic attenuation) applied to bone samples and conventional measurements of bone properties (such as BMD and Stiffness) of the samples to derive functional relationships between ultrasonic measurements and parameters and bone properties. These functional relationships are used to determine bone properties at bone sites for a live person via ultrasonic measurements and determination of ultrasonic parameters from those measurements.

The present invention also provides for scanning of two and three dimensional regions of the bone of a patient at step sizes and resolutions that correspond to the trabeculae. The determinations of bone properties such as BMD and Stiffness at this resolution offer further analysis over a region of the bone, including regression analysis of a region and visual imaging at the trabeculae level.

Accordingly, the invention comprises a system for determining at least one bone property of a bone sample at at least one point. The system includes a transmitting ultrasonic transducer and a receiving ultrasonic transducer, both transducers being confocal transducers. The transducers are configured to receive the bone sample therebetween such that the confocal point of the transducers are located at the at least one point in the bone sample. A processor initiates an ultrasonic signal from the transmitting transducers that is transmitted through the at least one point of the bone sample when positioned between the transducers. The ultrasonic signal is received by the receiving transducer and the processor in turn receives a signal reflecting one or more measures of the received ultrasonic signal. The processor determines at least one ultrasonic parameter for the at least one point of the bone sample based upon the transmitted and received ultrasonic signals. The processor further determines the at least one bone property at the point of the sample based upon the at least one ultrasonic parameter.

The invention is also applicable in a wide variety of applications where it is desired to detect mechanical properties of materials at a smaller level particularly where the material necessitates a nondestructive, noninvasive technique, even if the material has a nonhomogeneous structure. Such applications may include, for example, determining structural integrity of bridges, submarines, airplane-wings, etc., detection of skeletal healing, identification of masts or cysts in soft tissue. The methods and apparatus of the present invention find further application in smart drug delivery by precisely thermally activating ingested drugs utilizing the precision of the confocal targeting method of the present invention.

Accordingly, the invention also comprises method for determining at least one material property of a material sample at a point of interest. The method comprises emitting an ultrasonic signal such that it focuses at a confocal point. A material sample is positioned so that the ultrasonic signal passes through the material sample and such that the point of interest of the material sample lies within the confocal point of the ultrasonic signal. The ultrasonic signal is received after it passes through the material sample. At least one ultrasonic parameter is determined for the point of interest of the material sample based upon the transmitted ultrasonic signal and the received ultrasonic signal. In addition, the at least one material property at the point of interest of the sample is determined based upon the at least one ultrasonic parameter.

The invention comprises a system for determining at least one material property of a material sample at at least one point. The system includes a transmitting ultrasonic transducer and a receiving ultrasonic transducer, both transducers being confocal transducers. The transducers are configured to receive the material sample therebetween such that the confocal point of the transducers are located at the at least one point in the material sample. A processor initiates an ultrasonic signal from the transmitting transducers that is transmitted through the at least one point of the material sample when positioned between the transducers. The ultrasonic signal is received by the receiving transducer and the processor in turn receives a signal reflecting one or more measures of the received ultrasonic signal. The processor determines at least one ultrasonic parameter for the at least one point of the material sample based upon the transmitted and received ultrasonic signals. The processor further determines the at least one material property at the point of the sample based upon the at least one ultrasonic parameter.

Other characteristics and advantages of the present invention will emerge from the description given hereafter with reference to the attached drawings, which illustrate various examples of implementation and embodiments thereof, without any limiting character.

BRIEF DESCRIPTION OF THE DRAWINGS

The foregoing features of the present invention will become more readily apparent and may be understood by referring to the following detailed description of an illustrative embodiment of the present invention, taken in conjunction with the accompanying drawings, where.

DETAILED DESCRIPTION OF THE PREFERRED EMBODIMENTS

Abbreviations and Definitions

BUA means broadband ultrasonic attenuation and when measured a BUA value may be expressed as dB/MHz. Attenuation of broadband ultrasonic waves increases as soft tissue thickness increases that is less dense than the hard or calcified tissue.

Transmission mode comprises a longitudinal wave that is transmitted into the bone by a sending transducer, the wave traveling through the bone toward a receiving transducer, and being received by the receiving transducer which converts it into an electrical signal.

Transmission frequency generally refers to the characteristic frequency of the ultrasonic transducers in which the maximal acoustic energy is excited by electric-mechanic coupling, and reflects to the frequency of the acoustic wave that is being transmitted from the ultrasonic source. Transmission frequencies in the embodiments of the present invention typically range between 0.2 MHz and 25 MHz. Higher frequencies usually provide higher spatial resolution. Tissue penetration decreases with higher frequencies. Lower transmission frequencies are generally characterized by lower spatial resolution with improved tissue penetration.

Ultrasonic pulse includes any ultrasonic wave transmitted by an ultrasonic source. Typically, the pulse will have a predetermined amplitude, frequency, and wave shape. Ultrasonic pulses may range in frequency between 20 kHz and 20 MHz or higher in the embodiments of the present invention. Ultrasonic pulses may consist of sine waves with single frequency or varying frequencies, as well as single amplitudes and varying amplitudes. In addition to sine waves, square waves or any other wave pattern may be employed.

Explanation of Principle

Ultrasound is capable of non-invasively determining bulk trabecula strength. The present invention detects bone strength at a much smaller region or level, for example, trabeculae, and a defined volume, for example, two-dimension and three-dimension regions for the purpose of accurately predicting osteoporosis and risk of fracture.

The present invention overcomes a limitation that arises when ultrasound is applied in the measurement of smaller bone structures or regions. Specifically, the measurement of smaller bone structures requires increased frequency. However, an undesirable consequence of increasing the frequency of interrogation is that there is a corresponding increase in energy loss. To overcome this limitation, the present invention utilizes a relatively high frequency (for example in the range of 1-10 MHz) that can be used to examine smaller bone structure, along with confocal scanning to make up for energy losses due to the enhanced frequency.

In its application to produce ultrasound attenuation (UA) and velocity (UV) measurements, use is made of a pair of focused ultrasonic transducers, being of single element type, operating in transmission mode and being placed opposite one another, converging at a focal region and operating at a high characteristic frequency. For example, the transducers may operate in transmission mode at characteristic frequencies of 5, 7.5, 10, 15 and 20 MHz. The ultrasound transducer is made of PZT sandwiched between layers of gold and the focus lens may be a silicon composite material for better water coupling of ultrasound. The design of the transducer is such that, for example, the confocal point can be controlled to be approximately 0.5 mm in diameter, with focal length, for example, on the order of 10-50 mm. Preferably, measurements for use in the method of the invention are made over an area at a spacing (i.e., scanning step size or equivalent) between measurement locations of no more than 5 mm, more preferably at a spacing of from 0.1 to 1 mm, for example by scanning the pair of confocused ultrasonic transducers over the area. The resolution of the ultrasound scan may be further improved through micro-scanning and mapping in the regions of interest to avoid imprecisions associated with porous structures.

As specified herein above, the principle on which the method forming the subject of the invention is based resides in transmitting a high-resolution confocal ultrasound wave into a bony member and in studying the changes in properties of the wave after passing through the bone. The converged beam may be as fine as 0.5 mm in diameter in the focusing region. A pair of transducers, one for emitting and one for detecting are positioned in proximity to the bony member at points along an axis that passes through the focusing region.

Figure 1A:
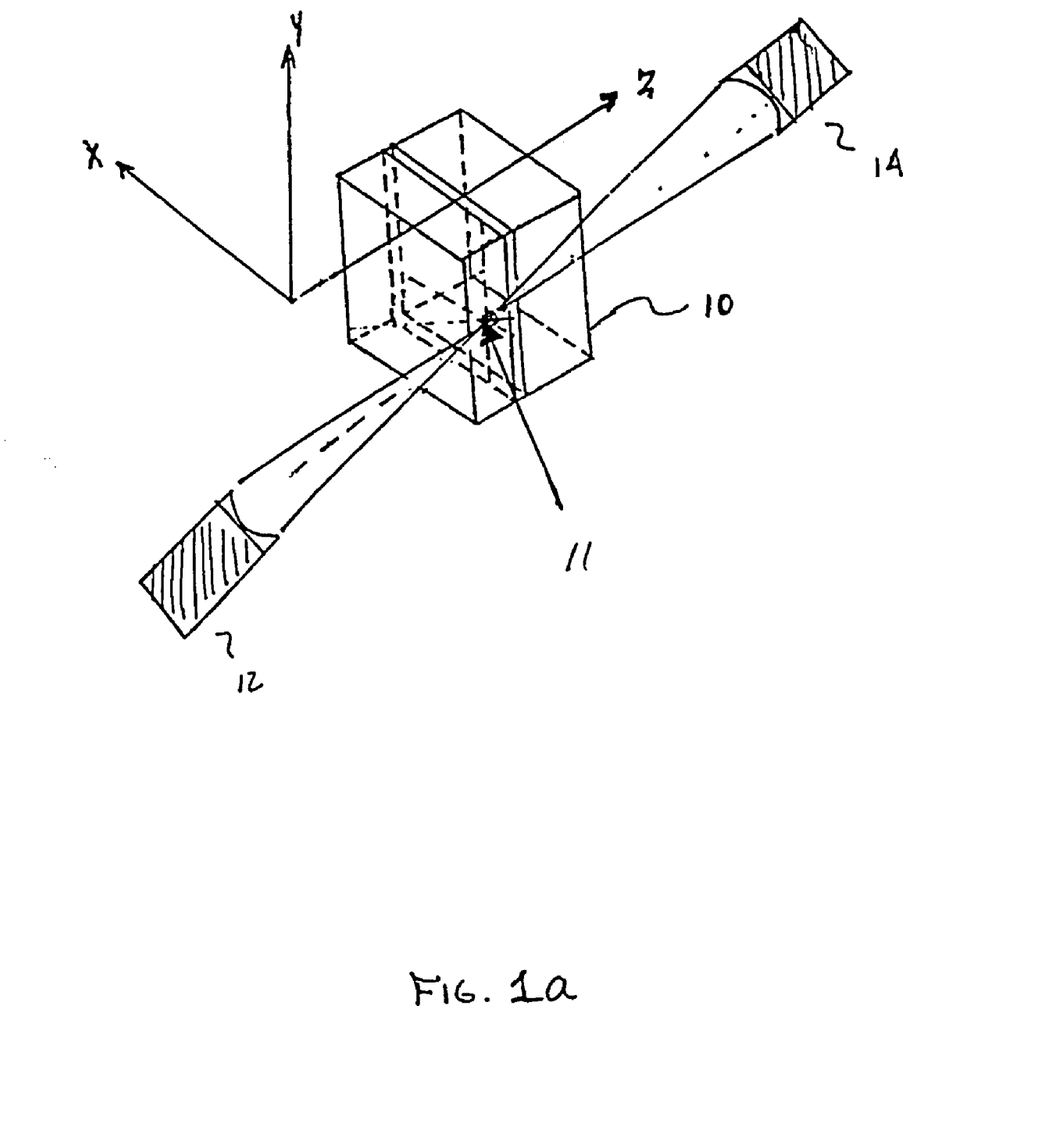
FIG. 1a is an illustration of how confocal scanning is performed in three-dimensions for a sample bone specimen.

FIG. 1a illustrates a bone specimen 10 and a pair of confocal transducers 12, 14 for performing an area or volume mechanical scan in accordance with the (x,y,z) co-ordinate system shown. A scanned image of the bone specimen 10 is generated in stages by displacement of the focused transducers 12, 14 under the action of a stepping motor (not shown).

When performing a bone scan, data may be acquired either discretely or continuously. In the discrete scanning mode, a computerized algorithm controls the time duration for each scanning step performed by a 3-D scanning stage. Each step is controlled as fine as approximately 0.1 mm.

In the discrete scanning mode, scanning is first performed in a translational stage wherein the focused transducers are moved in small steps or increments in an x-y plane orthogonal to the direction of the radiated confocal beam. The steps or increments are referred to as the scanning resolution. At each step or increment, the transducer pair 12, 14 makes an ultrasonic measurement at a confocal point 11 in the x, y, z plane. The confocal point or resolution represents the resolution of the ultrasonic wave at the convergence point (i.e., x. y, z) and is determined at the manufacturing stage as a function of the construction of the transducer pair 12, 14. It is noted that the confocal resolution is independent of the scanning resolution, however, they are generally of the same order. For example, as noted above, the confocal point may be on the order of 0.5 mm and the scanning resolution may be as fine as on the order of 0.1 mm. In this case, the confocal resolution envelops or captures five scanning steps. The peak of the confocal intensity will therefore be directed to a central scanning step with the adjacent scanning steps providing additional information.

In operation, in the discrete scanning mode at each step, one of the pair of focused transducers generates a brief pulse, on the order of 0.1 to 5.0 microseconds, of ultrasonic energy at a predetermined frequency which is focused to a point within the bone specimen, passes through the bone specimen and is received by the second transducer. Data is collected for that point and is stored for later analysis or analyzed immediately. After scanning a plane of the specimen, the focused transducer pair 12, 14 are advanced incrementally in a direction perpendicular to the acoustic axes of the focusing systems (i.e., the z-direction), and another x-y plane of the specimen is searched in like manner. Measurement in the z-direction also corresponds to a scanning step size, as described above. In this manner successive layers of the tissue are imaged.

In the continuous scanning mode, a plane is scanned continuously, in contrast to the incremental shifting described above for the discrete scanning mode. In the continuous scanning mode the transmitting transducer 12 and the receiving transducer 14 are moved continuously across a scanning line (for example, in the horizontal x direction) and interrogation pulses are continuously emitted from the transmitting transducer 12 and received by the receiving transducer 14. The ultrasonic data emitted and received by the transducers 12, 14 is correlated to the scanning position in the bone by a control computer 22. The computer 22 correlates the control (timing) signals sent to the stepper motor which is in turn correlated to a position on the bone specimen (x, y, z).

The continuous scan mode is performed much faster than the discrete mode, since the stepper mode sweeps continuously across a scanning line instead of stopping at each measurement point. The difference in the speed of measurement is the only substantive difference between the discrete and continuous modes. The measurement parameters are substantially the same in both modes.

Figure 1B:
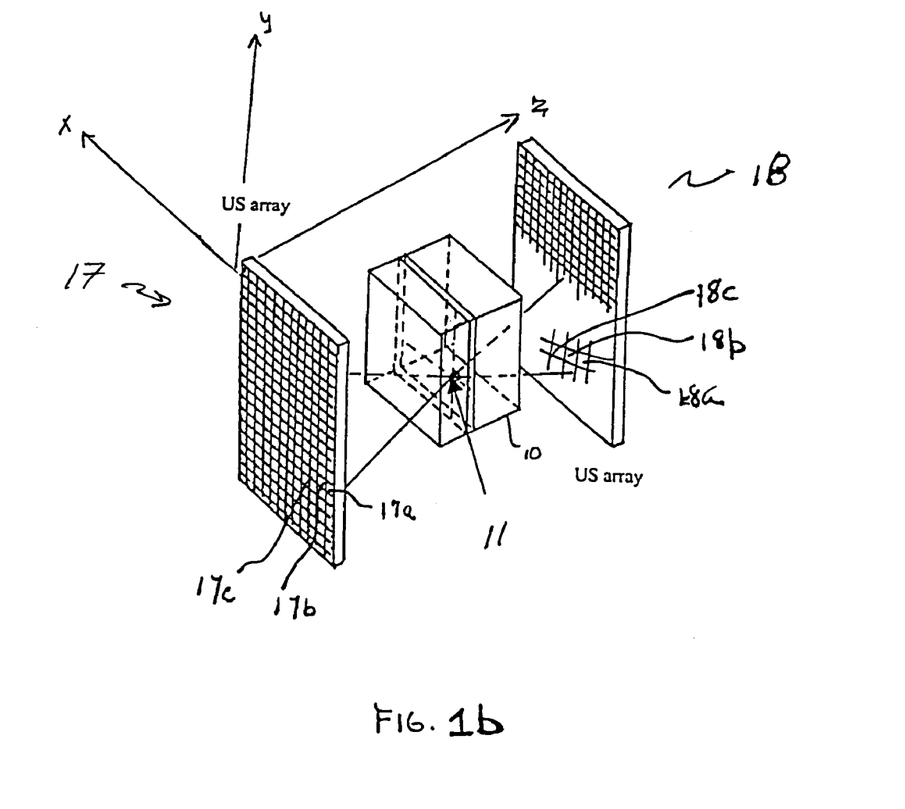
FIG. 1b is an illustration of an alternate embodiment for confocal scanning in three dimensions for a sample bone specimen.

The continuous and discrete scanning modes have been described above in the context of a mechanical scanning process whereby transducer elements are mechanically shifted either continuously or in discrete steps subsequent to making a measurement. In an alternate embodiment, the present invention may utilize electronic scanning wherein planar electronic transducer arrays substitute for the transducer elements 12, 14 that are mechanically moved, as described above. Confocal scanning of the bone sample is accomplished by emitting and receiving from the transducer elements in the emitting and receiving transducer arrays.

FIG. 1b illustrates a bone specimen 10 and a pair of electronic ultrasound confocal transducer arrays 17, 18 for performing an area or volume scan in accordance with the (x,y,z) co-ordinate system. For each point in the scan, electronic confocal scanning is performed by emission of ultrasonic pulses from the transducer emitting elements 17a, 17b, 17c, etc. and receipt by the corresponding transducer receiving elements 18a, 18b, 18c, etc. Pulses from each of the emitting elements 17a, 17b, 17c, etc. are coordinated electronically in magnitude, phase and time of emission so that the composite ultrasonic wave is focused at the particular point in the scan. The ultrasonic wave is captured by the receiving transducer array elements 18a, 18b, 18c, etc. after passing through the bone specimen and is processed by the system to give bone properties, such as density and stiffness, for the particular point in the scan. The properties of the ultrasonic wave used and the bone properties determined at each point are described in detail below. Scanning of the next point in the sample is achieved by electronically adjusting the emissions by the transducer elements 17a, 17b, 17c, etc. so that the confocal point of the composite wave lies at the next point. The confocal point is thus moved electronically in the x, y and z dimensions to perform a volume scan. After processing, the three dimensional data of bone properties may be used to create images for clinical viewing, for example.

Optionally, the processing step may identify one or more regions of interest (ROI) where the data for the points in the ROI indicates the bone property is outside normal parameters.

Scanning Confocal Acoustic Diagnostic (SCAD) System.

Figure 2:
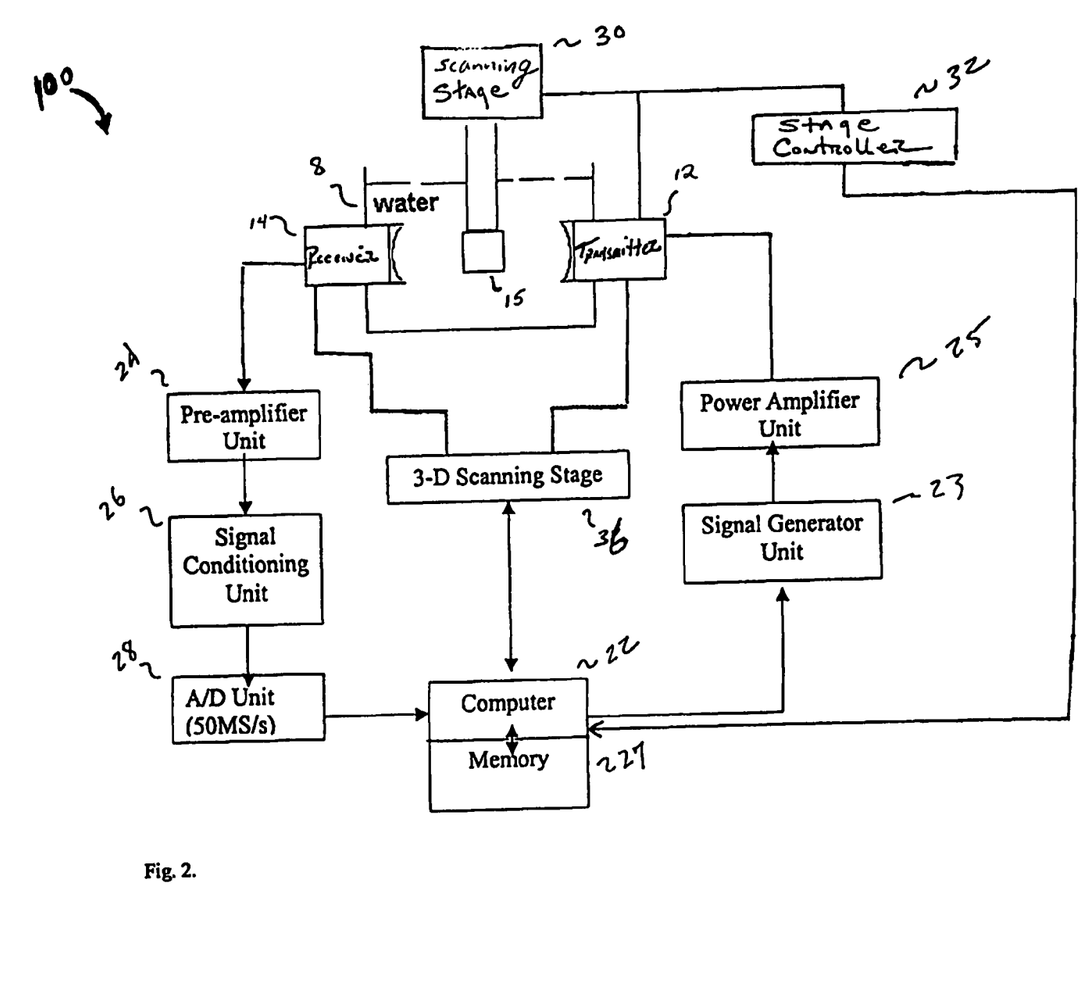
FIG. 2 is an overall block diagram of the scanning confocal acoustic diagnostic system according to the invention.

The invention is shown in FIG. 2 in application to interconnected components for constructing apparatus for performing methods of the invention, namely, for non-invasively and quantitatively evaluating the status of bone tissue, as manifested through one or more of the quantities: bone-mineral density, architecture, strength, and fracture risk at a given time. These components are, in general, commercially available from different sources and will be identified before providing detailed description of their total operation.

Referring to FIG. 2, it is seen that, in this non-limiting exemplary embodiment, the system implementing the method forming the subject matter of the invention is referred to herein as a scanning confocal acoustic diagnostic (SCAD) system generally designated as numeral 100. The SCAD system 10 essentially includes a generally box shaped measurement chamber 8. A transmitting 12 and receiving 14 transducer pair are positioned in the chamber 8 so that they extend into the chamber 8 to be on opposite sides of the bone sample 15 placed in the chamber 8. The bone sample 15 can be, for example, a person's heel bone, or a 1×1×1 cm bone specimen cube. The bone sample 15 attaches to a scanning stage 30 which is operated under computer control by a stage controller 32. The sample stage 30 is used to initially position the bone sample 15 in the chamber 8.

A coupling liquid is provided in the chamber 8 to provide a low loss path for acoustic energy between the transducers 12,14 and the bone sample 15 regardless of the dimensions of the latter. The coupling liquid is preferably water, but not limit to water, e.g., the coupling can use acoustic gel. A surfacant may be added to the water, which has been found to improve the signal quality, making it possible to take the measurements during immersion, the presence of the liquid medium ensuring good coupling between the ultrasound source and the bone, of which it is desired to evaluate, in particular, the mechanical properties. The surfacant may be, for example, a commercially available detergent. It will be recognized, however, that other flowable, acoustically conductive media may be used to provide acoustic coupling, and hence, that the term "coupling liquid" should be considered to embrace materials having a viscosity higher than that of water such as, for example, water based slurries and thixotropic gels.

Ultrasound measurements may be made by sending an ultrasound signal from the first or transmitting transducer 12 positioned at one side of a bone sample 15 to the second or receiving transducer 14 positioned at the opposite side of said bone sample 15. The transmitter/receiver transducer pair 12,14 is focused and converged at the confocal region/point, (see FIG. 1) the distance separating them being approximately equal to twice the focal length.

The transducer pair 12, 14 are specially designed focused piezoelectric ultrasound transducers operating in the frequency range substantially between of from approximately 0.2 MHz and 20 MHz. The ultrasound transducers are constructed of PZT sandwiched between layers of gold. The focus lens is made from silicon composite material to enhance water coupling of the ultrasound. The transducers are designed to create a confocal point of approximately 0.5 mm in diameter, also referred to as the confocal resolution, and have a focal length on the order of 10 mm to 50 mm.

To make an ultrasound measurement, the process begins with the signal generator unit 23 generating a voltage excitation signal. The excitation signal can be one of a broadband pulse, a frequency specific tone burst or both. The signal generator unit 23 may suitably be an embedded function unit in the system or an arbitrary function-generator including, for example generators from WaveTex Inc., DC, HP Inc., and Stanford Research System, Inc. Alternatively, the signal generator unit 23 can also be constructed as a customized generator design.

The generated signal is then amplified by power amplifier unit 25. The power amplifier 25 unit includes a high impedance signal output, and low noise single amplification capability. Alternatively, the power amplifier 25 can also be constructed as a customized unit. The amplified signal is then sent to the transmitting transducer 12 which emits the amplified ultrasonic wave (in general, a pulse having a pulse width between 0.1 and 5.0 microseconds) through the bone specimen 15 to be detected by the receiving transducer 14. The ultrasonic wave is focused at a point in the sample 15 as described above.

The ultrasound pulse thus radiated by transmitting transducer 12 is transmitted into the propagation medium. As has been specified hereinabove, the measurement can be carried out in immersion mode in order to obtain good coupling between the radiation source and the bone. Modification of the ultrasound wave's properties by the bone reflects the properties of the bone sample as described further below.

The receiving transducer 14 converts the detected waveform into an electrical signal which is amplified by pre-amplifier unit 24. Signal-filtering, gain control and other pre-process tasks are then performed by signal conditioning unit 26 and an analog-to-digital conversion unit 28 receives analog signals acquired in real time from the signal conditioning unit 26, and provides digital signal outputs to the embedded computer 22.

The computer 22 has associated therewith, an internal processor, a bulk memory 27 and a signal processing software package designed for analyzing the acquired data. The computer 22 may be a conventional microcomputer programmed to carry out the bone-value calculations by the algorithms discussed below, or a dedicated microprocessor. Computer 22 also includes algorithms to control operations of the system (such as the scanning by the transducers 12, 14) although this may be performed by a separate computer or controller. The design and operation of the computer 22 will become clear from the algorithms discussed below.

The system 100 of FIG. 2 may further include a digital oscilloscope (not shown) with General Purpose Interface Bus (GPIB) interface to transfer digital signals to the computer 22. The oscilloscope is used to output a visual representation of the acquired signals (i.e., output by the A/D converter 28 or otherwise provided by computer 22 for the sample locations scanned). Computer control of both the digitizing oscilloscope, the signal generator 23, and the stage controller 32 (which causes stage 30 to provide an initial position of bone sample 15 with respect to the positions of transducers 12, 14) are enabled via the GPIB, and a GPIB card in the computer 22. The GPIB and GPIB card may suitably be obtained from National Instruments. Inc., Austin, Tex.

The computer 22 performs the following functions and calculations: controlling the signal generator unit 23 by providing waveform data thereto and/or setting the rate of the pulse or tone burst and other miscellaneous control signals; independently controlling the movement (range and speed) of the three-dimensional scanning stage to perform a three-dimensional scan of a bone specimen (either discretely or continuously) as described above including coordinating the movement of the three-dimensional scanning stage to allow the three-dimensional scanning stage 36 to perform a two-dimensional scan of the x-y plane of the above specimen at a point z as described above; processing the received digitized ultrasound signals from the A/D unit 28 in time and frequency domain to generate ultrasound images; reconstructing the three-dimensional images or other representing forms of the sample data; calculation of the propagation times of the signals transmitted through the bone; calculation of the elastic modulus (E) (e.g., MP); calculation of the bone thickness passed through at the measurement location. Computer 22 also performs calculation of the propagation velocity of the ultrasound in transmission (UV); calculation of the ultrasound attenuation number (ATT) (in dB); calculation of the broadband ultrasound attenuation (BUA) (in dB/MHz), calculation of BMD and Stiffness, all as further described below.

It is, of course, possible to add other signal-processing or image-processing functions which can provide quantitative information that is useful for characterizing the bone.

Preferred Method of Operation

Prior to making measurements with the system of the present invention, a verification process is performed in which a number of bone quality coefficients are first determined and stored in a database in memory 27 or otherwise accessible by computer 22 and/or data library for later use when making measurements. It is further noted that the database may be updated at any time to accommodate verification processes that provide additional data for previously stored materials, or data related to different materials and/or structures.

The bone quality coefficients correlate the measured ultrasound parameters of ultrasound attenuation and velocity, i.e., UA and UV, measured in accordance with confocal transducers of the present invention, with known microstructural parameters measured (for example on a series of bone samples harvested ex vivo) via well known methods including micro computer tomography and mechanical testing. Conventional measurements of one or more test bone samples using known methods include testing for both structural density and mechanical moduli using conventional micro-computer tomography (micro-CT), at a resolution of 40 microns, porosity, trabecular thickness and trabecular space, and contact mechanical strength in three orthogonal directions, and ultrasonic attenuation and velocity in three orthogonal directions, i.e., longitudinal, med-lat and ant-post. The conventional measurement results are then compared with measurements of ultrasound velocity (UV) and ultrasound attenuation (UA) made on the one or more test samples using the confocal transducers of the present invention to determine a number of independent regression coefficients. The coefficients are then used to formulate mathematical equations which relate the measured values of ultrasound velocity (UV) and ultrasound attenuation (UA) made in accordance with the method of the present invention with the desired bone quality parameters of interest including bone mineral density (BMD) and stiffness.

In particular, using linear or non-linear regression analysis, the measured ultrasound parameters including ultrasound velocity (UV) and the broad ultrasound attenuation (BUA) measure of UA at a location (x,y,z) are compared to bone mass density (BMD) values measured via conventional micro-CT techniques to determine a number of independent regression coefficients. Once determined, the regression coefficients are stored in a database and/or data library accessible by computer 22 (for example, stored in memory 27) to be later recalled and used to formulate mathematical equations which relate the measured values of ultrasound velocity (UV) and broadband ultrasound attenuation (BUA), made in accordance with the method of the present invention, with the desired bone quality parameters of interest including bone mineral density (BMD) and stiffness.

Using linear or non-linear regression analysis in this manner, equations which relate the measured values of UV and BUA to BMD and stiffness are:

$$BMD = e + f*UV + g*BUA \quad (1)$$

$$Stiffness = l + m*UV + n*BUA \quad (2)$$

for a linear regression analysis.

$$BMD = a + b*UV + c*BUA + d*UV^2 \quad (3)$$

$$Stiffness = h + i*UV + j*BUA + k*UV^2 \quad (4)$$

for a non-linear regression analysis.

As noted, independent regression coefficients e, f and g are determined in a linear regression relating UV and BUA measured using confocal ultrasonic transducers on bone samples to BMD values of the samples measured using micro-CT techniques and other conventional techniques. Similarly, independent regression coefficients l, m and n are determined in a linear regression relating UV and BUA measured using confocal ultrasonic transducers on bone samples to stiffness values of the samples measured using micro-CT and other conventional techniques. Regression coefficients a, b, c and d and h, i, j and k are determined likewise using non-linear regression analysis. Each of the regression coefficients, i.e., (a-n) are constants for the particular material analyzed (such as above).

Stiffness and BMD can also be calculated from the UV and another measure of ultrasound attenuation, namely ultrasonic attenuation number (ATT), in accordance with the following equation:

$$Stiffness = p + q*UV + r*ATT \quad (5)$$

where UV represents the ultrasonic velocity path through the objective; ATT represents the broadband attenuation number and parameters p, q and r are the regression determined constants defined by experimental analysis based upon correlating UV and ATT measurements of samples with conventional measurements, analogous to that described above.

The bone mineral density (BMD) can also be calculated from the UV and ATT parameters in accordance with the following equation:

$$BMD = u + v*UV + w*ATT \quad (6)$$

where u, v and w are linear regression determined constants based upon correlating UV and ATT measurements of samples with conventional measurements, analogous to that described above.

In general, the regression coefficient constants in the above equations may be updated and refined further, for example, by using more samples or by improvements in measuring equipment.

The mathematical equations which more fully describe the relationship of BMD and Stiffness to the measured values of UV, BUA and ultrasonic attenuation number ATT (another measure of UA) are described in detail below.

It has been determined that the verification procedure described above typically yields correlation values greater than 0.7, where the correlation values represent a correlation between the predictive UA and UV values, measured in accordance with the method of the present invention, and BMD values measured via micro-CT and other conventional measures. While ultrasound attenuation (UA) and ultrasound velocity (UV), measured in accordance with the method of the present invention, both individually correlate well to bone mineral density (BMD) and stiffness, it has also been determined that the correlations were significantly improved using the combined parameters of ultrasound attenuation (UA) and velocity (UV), i.e., yielding correlation values greater than 0.8. It has also been shown that correlation values in excess of 0.71 was achieved between the predictive UA and UV values measured in accordance with the invention and bone stiffness.

Figure 3:
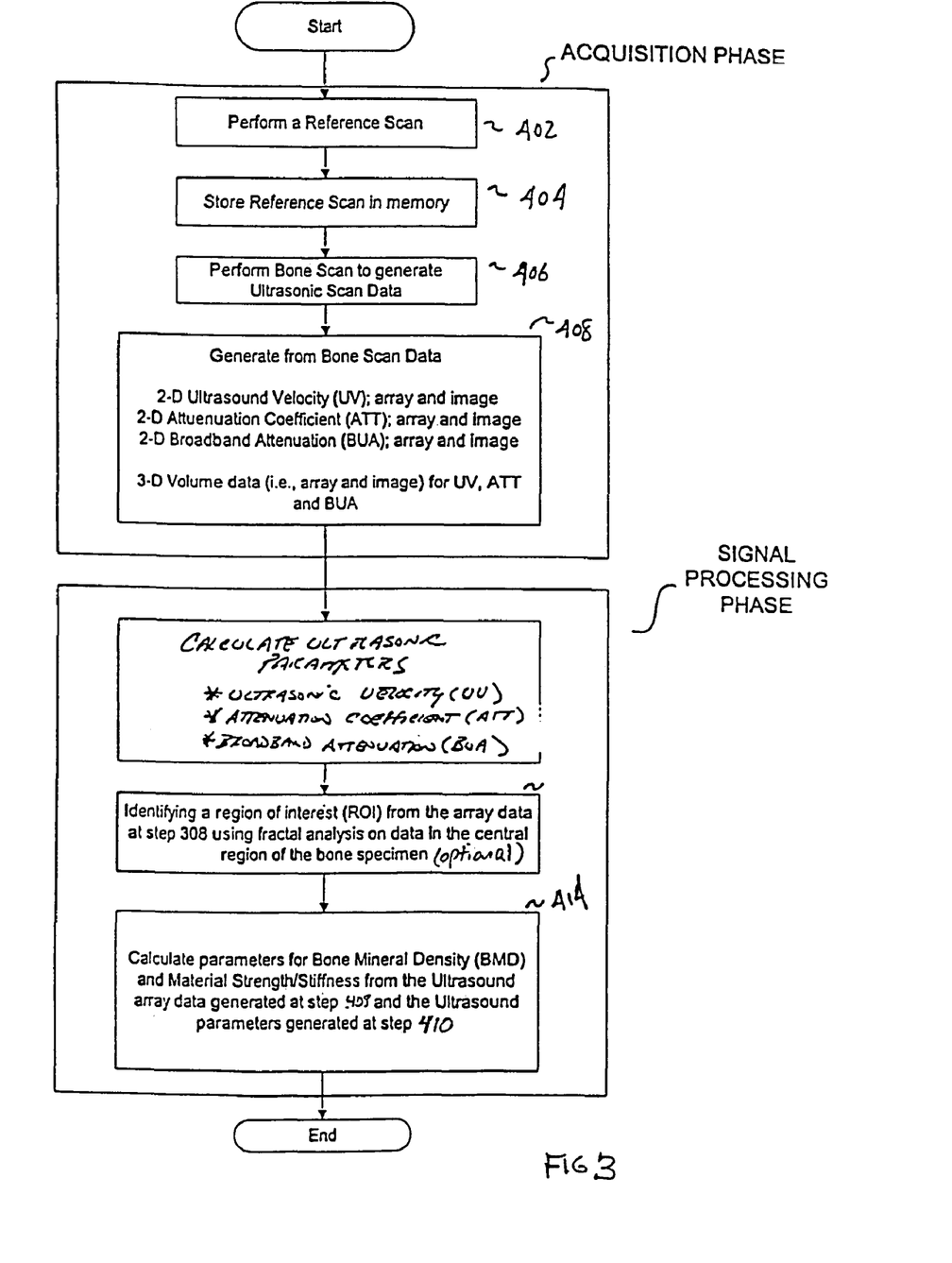
FIG. 3 is a flowchart illustrating one embodiment of the invention relating to methods of interrogating a bony structure according to the invention.

FIG. 3 is a flowchart illustrating one embodiment of the invention relating to methods of analyzing a bony structure and strength. As will be understood from the figure, the processing of present embodiment may be broadly separated into two stages, i.e., an acquisition stage and a signal processing stage.

First, at step 402, signal acquisition is initiated by performing a reference scan. The reference scan is performed by emitting a broadband reference ultrasound pulse from the transmitting transducer 12 prior to the bone specimen scan. The reference scan is performed with only the acoustic coupling medium between the two ultrasound transducers 12, 14.

The reference scan uses the same input excitation signal, scan dimension, and scan resolutions used for generating the scan in the bone specimen.

At step 404, a reference scan return signal received by the receiving transducer 14 is digitized by the A/D unit 28 and stored in the computer memory 27. The stored reference pulse return signal serves as a baseline for subsequent calculation for the measurements of the bone quality.

Next at step 406, a bone scan is performed. It is first noted that when performing a bone scan, data may be acquired in this embodiment using a mechanical scan, which is either discrete or continuous, as described above. In a discrete scanning mode, a computerized algorithm controls the time duration for each scanning step performed by the 3-D scanning stage 36. Each step can be controlled as fine as 0.1 mm. In a continuous scanning mode, the region of interest is scanned continuously line by line and shifts one increment to the neighboring plane in the region of interest of the specimen. In the continuous scanning mode, the computer correlates the control steps sent to the stepper motor with emission and reception of ultrasonic pulses to segment the pulses corresponding to distinct positions in the bone specimen. A high speed A/D device 28 is used in this scanning mode having a resolution of 100 MHz or higher. For convenience, the description the below will use the "step" terminology more closely associated with the discrete scan, but may also be considered the ascribed points in the continuous scan.

A bone scan is performed by moving the transducers 12, 14 synchronously in the horizontal (x) and vertical (y) directions to scan over an area for a fixed z (see FIG. 1). As the transducers move, signals are emitted from one transducer and are received by the other transducer for each sample location (x,y,z). The bony specimen is initially positioned in the apparatus prior to initiating the bone scan. The transducers 12, 14 are positioned, under computer 22 control, preferably at the upper left corner of the bone specimen. Confocal scanning is performed initially in a two-dimensional plane (e.g., x-y plane from left to right) parallel to the plane of the movement of the transducers to generate a 2-D data array of ultrasound attenuation and velocity coefficients (i.e., a UA image and a UV image) in the memory of computer 22. As the transducers 12, 14 are moved in a horizontal scan line, ultrasonic pulses and data are emitted and collected for each step (point) in the line. As noted, for the discrete scan the step corresponds to discrete displacement of the transducers whereas for the continuous mode it corresponds to an ascribed postion in the scan line over which a segment of the ultrasound is emitted. Upon completion of one horizontal scan (in x), the transducers are moved downward in a predetermined increment (in y) to perform a second horizontal scan. The scan procedure is performed, scan-line by scan-line until an entire 2-D region of interest is scanned (an x-y plane within the specimen at the confocal point in z). Ultrasonic data collected for each step point (x,y,z) in the bone specimen, where z is the location of the confocal point on the z axis.

A three-dimensional image may be formed from the 2-D by moving the transducer pair 12, 14 in the direction vertical to the scanning plane (z) thereby shifting the confocal plane along the axis between the transducers within the bone specimen (as shown in FIG. 1) and repeating the procedure for performing a 2-D planar scan. This process is repeated until the entire desired volume of the bone specimen is scanned and the array of data for points (x,y,z) of the bone sample is stored in memory 27. The scan data, such as $\Delta T$ and other measured parameters corresponding to the points in the bone sample described below, is stored in memory 22.

From the acquired ultrasonic signal data emitted and received for each scan point (x,y,z) in the specimen, values are calculated by the computer for the ultrasound velocity (UV), and one or more measures of ultrasonic attenuation (UA) such as ultrasonic attenuation number (ATT) and/or broadband ultrasound attenuation (BUA). It is noted that that the characteristic frequency range of the ultrasound transducers 12, 14 is substantially between 0.2 MHz and 20 MHz. Different frequencies inside the range may be used at different sites of the tissue when performing a measurement, in order to maximize or optimize detection resolution. Optimal frequencies for use may be predetermined during verification, i.e., in a series of in vitro and in vivo testing. The computer 22 may then display the values as images on a screen.

At step 408, three values may be generated by computer 22 using the emitted and received ultrasonic wave at each scan point (x, y, z) of the bone sample: a broadband ultrasonic attenuation (BUA) value, an ultrasound attenuation number (ATT) value, and an ultrasound velocity (UV) value. The BUA and ATT values represent two different forms of ultrasound attenuation (UA). BUA represents the slope of attenuation as a function of frequency. The ultrasound velocity (UV) image represents the ultrasonic velocity through the bone specimen. Ultrasound attenuation number (ATT) image represents the energy decay attenuation as a function of material density. Generation of BUA, ATT and UV by computer 22 from the various scan data acquired and stored in memory 27 is further described below.

Ultrasound Velocity (UV) Value Generation

Ultrasound velocity (UV) provides one indication of the bone density (BMD) and mechanical stiffness of the bone specimen under study. Higher ultrasound velocity correlates to higher bone density and mechanical stiffness. The ultrasound velocity (UV) values determined at each scanning point collectively constitute a UV image of the bone specimen.

The measurement of ultrasound velocity (UV) is indirect for an embodiment that utilizes immersion of the bone specimen, as described in FIG. 1. As noted above, a reference scan is first performed (see step 402) wherein the delay of ultrasound in water from emitting transducer to receiving transducer without a bone sample is recorded. The delay for an ultrasound pulse to traverse a bone specimen is measured by comparing the bone traversing signal waveform with the waveform of the reference scan. A typical point of comparison can be the starting point of a rising edge, a point where the waveform crosses a threshold or zero crossing points of the waveform. The difference in position of such points on the time axis gives the time delay, $\Delta T$.

Subsequent to performing a reference scan at step 402, with the bone specimen inserted, the delay is measured at scanning points (x,y,z) in the specimen as described above. The ultrasound velocity (UV) at each point in the specimen is calculated indirectly from the difference of the delays $\Delta T$ between the reference and bonescan data for that point, the thickness of bone w and the ultrasound velocity in water $v_w$. Equation (7) describes the ultrasound velocity calculation performed by the computer 22 at each scanning point (x,y,z) of the bone specimen.

$$UV_{(x,y,z)} = v_w * w / (w - v_w * \Delta T) \quad (7)$$

For the UV image generation, $\Delta T$ is the delay at point (x,y,z) as determined by the scan data, while w and $v_w$ are input or stored parameters.

ATT Value Generation

The ultrasound attenuation number (ATT) is calculated as the ratio of two ultrasound response signals, the reference signal discussed above and a bone specimen signal. The ratio is calculated at each scanning point (x,y,z) of the bone specimen as:

$$ATT_{(x,y,z)} = 10*LOG[(\text{energy of reference signal})_{(x,y,z)}/(\text{energy of bone signal})_{(x,y,z)}] \quad (8)$$

It is noted that the ultrasound attenuation number (ATT) calculated through equation (8) is a numerical value which is neither a function of time or frequency. The energy of the emitted signal that passes through the bone, thus generating bone signal at each point must originally have the same energy as the reference signal, or otherwise be normalized with respect to the energy of the reference signal. The ATT values determined by computer 22 based on ultrasound signal data at each scanning point (x,y,z) collectively constitute an ATT image.

BUA Value Generation

Broadband ultrasound attenuation (BUA) is a function of frequency. Specifically, it is the slope of the linear section of the ultrasound attenuation coefficient function, UAC(f). The UAC(f) is calculated from the fast fourier transform (FFT) of frequency (as a function of time) for the reference and bone scan signals in accordance with the following equation:

$$UAC_{(x,y,z)}(f) = 20 \log[(FFT(f_{ref}(t))/(FFT(f_{bone}(t))] \quad (9)$$

Then, BUA is determined as the slope of the linear section of UAC(f). The preferred frequency domain where the linear section resides is between 300 kHz and 700 kHz. The broadband ultrasound attenuation (BUA) values determined by computer 22 from the ultrasound signal data at each scanning point (x,y,z), in accordance with equation (9), collectively constitute a BUA image.

Additional Signal Processing for Determining Bone Properties

At step 414, the stiffness and/or the bone mineral density (BMD) are calculated by computer 22 for each point (x,y,z) using the equations developed above, i.e., eqs. 1-6, along with the previously determined regression coefficients. The stiffness may be computed from the UV and BUA values determined (as described immediately above) and stored in accordance with the following equation:

$$\text{Stiffness} = h + i*UV + j*BUA + k*(UV)^2 \quad (10)$$

where UV represents the ultrasonic velocity at each point as described above; BUA represents the broadband ultrasound attenuation at each point as described above and parameters h, i, j and k are the non-linear regression determined constants discussed above, (see Eq. 4).

In the case of trabecular bone material, these constants will generally fall in the ranges shown in Table I.

TABLE I

| h | i | j | k |
|---|---|---|---|
| −10000.0~1000.0 | −1.0~10.0 | −10.0~0.1 | $-10^{-4} \sim 10^{-3}$ |

Stiffness can be alternatively calculated as a first order equation as:

$$\text{Stiffness} = l + m*UV + n*BUA \quad (11)$$

where l, m and n are linear regression determined constants as discussed above, (see Eq. (2)). In the case of trabecular bone material, these constants are generally in the ranges shown in Table II.

TABLE II

| l | m | n |
|---|---|---|
| −500.00~+500.00 | −0.1~10.0 | −10.0~0.1 |

The bone mineral density (BMD) may be computed for each point (x,y,z) in the bone specimen from the UV and BUA values collected for each point using the equations developed above, (see Eq. (3)) along with the previously determined regression coefficients:

$$BMD = a + b*UV + c*BUA + d*UV^2 \quad (12)$$

where UV is the ultrasonic velocity path at each point as described above through the specimen; BUA is the broadband ultrasound attenuation at each point as described above; and parameters, a, b, c & d, are regression determined constants.

In the case of trabecular bone material, these constants generally will fall within the ranges showing in Table III.

TABLE III

| a | b | c | d |
|---|---|---|---|
| 0.1~10.0 | −0.1~0.01 | −0.01~0.01 | $-10^{-7} \sim 10^{-6}$ |

BMD can be alternatively calculated as a first order equation as:

$$BMD = e + f*UV + g*BUA \quad (13)$$

where e, f, and g are linear regression determined constants, (see Eq. (1) above). In the case of trabecular bone material, these constants are in the ranges showing in Table IV.

TABLE IV

| e | f | g |
|---|---|---|
| −1.5~1.5 | −0.1~0.01 | −0.01~0.01 |

Stiffness at each point can alternatively be calculated from the UV and ATT values generated for each point in accordance with equation (5) developed above:

$$\text{Stiffness} = p + q*UV + r*ATT \quad (14)$$

where UV and ATT are as previously described and parameters p, q and r are the constant regression coefficients defined by experimental analysis and can be updated.

In the case of trabecular bone material, regression coefficients p, q and r are generally within the ranges shown in Table V.

TABLE V

| p | q | r |
|---|---|---|
| −2000.0~0.0 | 0.1~1.0 | −20.0~−1.0 |

BMD at each point can also be calculated from the UV and ATT values generated at each point in accordance with the following equation:

$$BMD = u + v*UV + w*ATT \quad (15)$$

where u, v and w are linear regression determined constants as described above (see Eq. 6). In the case of trabecular bone material, these regression coefficients u, v and w generally fall within the range shown in Table IV.

TABLE VI

| u | v | w |
|---|---|---|
| −500~1000 | 0.1~2.0 | −50.0~0.0 |

The stiffness and BMD values may be calculated in like manner for other points (x,y,z) in the three-dimensional scan based on the received ultrasonic signal and the initial generation of values of UA and BUA. The values of stiffness and/or BMD for each point may be stored in memory 27 as an array image for further analysis, including generation of a 3-D image that reflects stiffness and BMD at each point. The processing of the image signals for the points in the scan may occur as the scan is processed. In that case, some of the ultrasonic signal data for subsequent points may need to be buffered in memory 27 while the calculation of UA, ATT, BUA, stiffness and BMD are performed for prior points in the scan. Alternatively, partial processing of the signal data may be performed while the scan proceeds and stored for later processing. For example, values of UA, ATT and BUA may be generated during the scan and stored for each point. After the scan is complete, the stored values for UA, ATT and BUA may be retrieved to generate values of stiffness and BMD at each point.

In general, the computer 22 is programmed to calculate a value of Stiffness and/or BMD using one or more of equations 10-15. If Stiffness is calculated, generally only one equation is used by the computer 22 in the calculation, such as Eq. 10, Eq. 11 or 14. However, separate values of Stiffness may be calculated using two or more of Eqs. 10, 11 and 14 and, for example, an average Stiffness value may be calculated at each point. Likewise, if BMD is calculated by computer 22, generally only one equation is used by computer 22, such as Eq. 12, 13 or 15. Again, separate values of BMD may be calculated using two or more of Eqs. 12, 13 and 15 and, for example, an average BMD value may be calculated for each point. The equation or equations used by computer 22 to calculate Stiffness and/or BMD determine whether BUA or ATT (or both) must first be calculated from the ultrasonic data at each point. (UV is found in all of Eqs 10-15 and thus must be calculated for each point.)

The array of values of Stiffness determined for points (x,y,z) of the bone sample collectively comprise a stiffness image of the specimen. The data comprising the image may be processed to determine regions of interest (such as weak regions in the sample), formatted into a display format that visually identifies regions of like stiffness or other like processing. The array of values of BMD determined for points (x,y,z) of the bone sample likewise collectively comprise a BMD image of the specimen that may be processed in like manner.

In addition, to evaluate material's structural and material strengths, a new index may be generated for defining materials' quality. Material quality, i.e., trabecular bone quality, can be defined as a function of material structural density and material stiffness. Using the scanning confocal ultrasound method in bone as described above, an index, which includes both density and stiffness components, can be generated at each scanning point on the sample for predicting bone's quality. This index can be used for evaluating the quality of the material and predicting the risk of fracture. This index number may combine normalized BUA and Stiffness parameters generated from the ultrasonic measurements. Considering the rationale contributions of BUA and Stiffness to the bone quality, the index can be calculated as follows:

$$\text{Bone Quality Index.} = 0.7\, BUA/\beta + 0.3\, \text{Stiffness}/\tau \quad (16)$$

Where BUA and Stiffness is determined in one of the manners described above at each point, $\beta$ is a BUA normalization coefficient, and $\tau$ is a Stiffness normalization coefficient. Specifically, in the case of trabecular bone quality, the range of $\beta$, and $\tau$ is dependent on the sites of bone and cross different animals and will generally fall within the following ranges.

| β | τ |
|---|---|
| 100~200 | 300~600 |

The threshold for this index may be at 1, which the index above one could consider the material quality "good" or "strong," and the index below 1 is considered "weak."

Alternate Embodiment

In one particular embodiment, a determination of bone properties (e.g., bone mineral density, stiffness) is performed using fractal analysis. In accordance with this embodiment, a fractal analysis is performed by calculating an information dimension. The information dimension is a type of fractal dimension and can provide a reasonable indication of bone properties such as BMD or stiffness.

The information dimension is generally determined using one of the ultrasound images, i.e., BUA, UV and ATT, acquired in a manner described above. A procedure for calculating the information dimension is as follows. A first step for determining the information dimension is to make a threshold determination on an acquired image in either one, two or three dimensions. The threshold determination transforms the acquired image into a "black and white" image, where each pixel has a value of either 1 or 0, representing trabecular material or marrow cavity. Then, the transformed image is divided into subsections of predefined size $\epsilon \times \epsilon$.

A probability is calculated for each sub-section as follows:

$$P_i = \frac{N_i}{N_0} \quad (17)$$

where $N_i$ is the number of pixels of value 1 in the subsection i and $N_0$ is the total number of the pixels of the image. The information entropy for the subsection size $\epsilon$ is defined as $I(\epsilon)$:

$$I(\epsilon) = -\Sigma P_i \log(P_i) \quad (18)$$

where the summation is over all of the subsections i. The information dimension is determined as:

$$d_I = \lim_{\varepsilon \to 0} \frac{I(\varepsilon)}{\log\left(\frac{1}{\varepsilon}\right)} = \lim_{\varepsilon \to 0} \frac{\sum P_i \log(P_i)}{\log(\varepsilon)} \qquad (19)$$

As shown in equation (19), the information dimension is calculated as a single non-integer value whose range is dependent upon whether the calculation is performed in one, two or three dimensions. In one dimension, the information dimension is a non-integer value in the range from 0 to 1, where a number closer to 1 represents a more desirable result (i.e., healthier bone). Similarly, in two and three dimensions, the information dimension is calculated as a non-integer value in the range of 1 to 2, and 2 to 3, respectively.

Fractal Analysis is well known in the art and is discussed in Chaotic and Fractal Dynamics: an Introduction for Applied Scientists and Engineers, by Francis C. Moon, 1992, John Wiley & Sons, New York, incorporated herein in its entirety.

While the invention is susceptible to various modifications and alternative forms, specific embodiments thereof have been shown by way of example in the drawings and have been described in detail. It should be understood, however, that it is not intended to limit the invention to the particular forms disclosed, but on the contrary, the intention is to cover all modifications, equivalents and alternatives falling within the spirit and scope of the invention as defined by the appended claims.

What is claimed is:

1. A system for determining at least one bone property of a bone sample at least one point, the system comprising:
   a) a transmitting ultrasonic transducer and a receiving ultrasonic transducer, both transducers being confocal transducers, the transducers configured to receive the bone sample therebetween such that the confocal point of the transducers are located at the at least one point in the bone sample; and
   b) a processor configured to initiate an ultrasonic signal from the transmitting transducers that is transmitted through the at least one point of the bone sample when positioned between the transducers and received by the receiving transducer, the processor receiving a signal reflecting one or more measures of the received ultrasonic signal, the processor determining at least one ultrasonic parameter for the at least one point of the bone sample based upon the transmitted and received ultrasonic confocal signals, the processor further determining the at least one bone property at the point of the sample based upon the at least one ultrasonic parameter.

2. The system as in claim 1, wherein the confocal point of the transmitting and receiving transducers has a resolution equal to approximately 0.5 mm.

3. The system as in claim 1, wherein the transmitting transducer emits ultrasonic signals at a frequency on the order of tens of megahertz.

4. The system as in claim 1, wherein the system further comprises a three dimensional scanning stage on which the transmitting and receiving transducers are mounted, the three dimensional scanning stage moving the transmitting and receiving transducers in three dimensions to move the confocal point of the transducers to correspond to a number of points in the bone sample when positioned between the transmitting and receiving transducers.

5. The system as in claim 4, wherein, for each point in the bone sample corresponding to movement of the confocal point, the processor initiates an ultrasonic signal from the transmitting transducers that is transmitted through the bone sample and received by the receiving transducer, the processor receiving a signal reflecting one or more measures of the received ultrasonic signal, the processor determining at least one ultrasonic parameter for each point in the sample based upon the transmitted and received ultrasonic signals, the processor further determining the at least one bone property at each point of the sample based upon the at least one ultrasonic parameter for the point.

6. The system as in claim 5, wherein the three dimensional scanning stage performs a discrete scan.

7. The system as in claim 5, wherein the three dimensional scanning stage performs a continuous scan.

8. The system as in claim 4, wherein each point in the bone sample is separated by 0.1 mm.

9. The system as in claim 1, wherein the at least one ultrasonic parameter determined for the at least one point of the sample are ultrasonic velocity (UV) and a measure of ultrasonic attenuation (UA).

10. The system as in claim 9, wherein UV at the at least one point (x,y,z) of the sample is calculated by the processor as:

$$UV_{(x,y,z)} = v_m * w / (w - v_m * \Delta T)$$

where $\Delta T$ is the delay between the received ultrasound signal as passed through the bone sample and a reference ultrasound signal received without the sample positioned between the transducers, w is the thickness of bone and $v_m$ is the velocity of ultrasound in ultrasound velocity in a medium in which the bone is immersed.

11. The system as in claim 9, wherein the measure of UA is one selected from the group of broadband ultrasonic attenuation (BUA) and ultrasonic attenuation number (An).

12. The system as in claim 11, wherein the measure of UA is BUA, where BUA at the at least one point (x,y,z) of the sample is calculated by the processor as the slope of the linear section of the ultrasound attenuation coefficient function, $UAC_{(x,y,z)}(f)$, where $UAC_{(x,y,z)}(f)$ is calculated from the fast fourier transform (FFT) of frequency f (as a function of time) for the received ultrasound signal $f_{bone}(t)$ as passed through the bone sample and a reference ultrasound signal $f_{ref}(t)$ received without the sample positioned between the transducers in accordance with the following equation:

$$UAC_{(x,y,z)}(f) = 20 \log [(FFT(f_{ref}(t))/(FFT(f_{bone}(t))].$$

13. The system as in claim 11, wherein the measure of UA is ATT, where ATT at the at least one point (x,y,z) of the sample is calculated by the processor from the energy of the received ultrasound signal as passed through the bone sample and the energy of a reference ultrasound signal received without the sample positioned between the transducers in accordance with the following equation:

$$ATT_{(x,y,z)} = 10 * LOG [(\text{energy of reference signal})_{(x,y,z)} / (\text{energy of bone signal})_{(x,y,z)}].$$

14. The system as in claim 11, wherein the at least one bone property determined at the at least one point is bone mineral density (BMD).

15. The system as in claim 14, wherein BMD is determined at each point by at least one equation selected from the following group of three equations:

$$BMD = e + f * UV + g * BUA \qquad \text{i)}$$

$$BMD = a + b * UV + c * BUA + d * UW \qquad \text{ii)}$$

$$BMD = u + v * UV + w * ATT, \qquad \text{iii)}$$

where e, f and g; a, b, c and d; and u, v and w are constant coefficients, and UV, BUA and ATT are determined for the at least one point of the sample.

16. The system as in claim 15, wherein i) e, f and g are linear regression constants predetermined by conducting a regression analysis between measurements of UV and BUA on bone specimens and BMD measurements on the bone specimens using conventional analysis; ii) a, b, c and d are non-linear regression constants predetermined by conducting a regression analysis between measurements of UV and BUA on bone specimens and BMD measurements on the bone specimens using conventional analysis; and iii) u, v and w are linear regression constants predetermined by conducting a regression analysis between measurements of UV and AU on bone specimens and BMD measurements on the bone specimens using conventional analysis.

17. The system as in claim 11, wherein the at least one bone property determined at the at least one point is Stiffness.

18. The system as in claim 17, wherein Stiffness is determined by at least one equation selected from the following group of three equations:

$$\text{Stiffness} = l + m*UV + n*BUA \qquad \text{i)}$$

$$\text{Stiffness} = h + i*UV + j*BUA + k*(UV)^2 \qquad \text{ii)}$$

$$\text{Stiffness} = p + q*UV + r*ATT \qquad \text{iii)}$$

where l, m and n; h, i, j and k; and p, q and r are constant coefficients, and UV, BUA and ATT are determined for the at least one point of the sample.

19. The system as in claim 18, wherein i) l m and n are linear regression constants predetermined by conducting a regression analysis between measurements of UV and BUA on bone specimens and Stiffness measurements on the bone specimens using conventional analysis; ii) h, i, j and k are non-linear regression constants predetermined by conducting a regression analysis between measurements of UV and BUA on bone specimens and Stiffness measurements on the bone specimens using conventional analysis; and iii) p, q and r are linear regression constants predetermined by conducting a regression analysis between measurements of UV and ATT on bone specimens and Stiffness measurements on the bone specimens using conventional analysis.

20. A method for determining material properties of a bone, the method comprising the steps of:
 a) placing the bone between confocal ultrasonic transducers such that a confocal point is variously positioned on the bone, and transmitting an ultrasonic signal focused at the confocal point;
 b) positioning the bone so that the ultrasonic signal passes through the bone and such that a point of interest of the bone lies within the confocal point of the transmitted ultrasonic signal;
 c) receiving the ultrasonic signal after the signal passes through the bone;
 d) determining at least one ultrasonic parameter of the bone at the point of interest based upon the transmitted ultrasonic signal and the received ultrasonic signal;
 e) determining at least one material property at the point of interest of the bone based upon the at least one ultrasonic parameter;
 f) repositioning the confocal point to another point of interest in the bone;
 g) repeating steps ac to determine additional material properties of the bone; and
 h) repeating steps f and g to detect a region of interest in the bone based upon the detected material properties.

21. The method as in claim 20, wherein the confocal point is not greater than 0.5 mm.

22. The method of claim 21, wherein determining at least one ultrasonic parameter for the point of interest of the bone comprises determining the ultrasonic velocity (UV) and a measure of ultrasonic attenuation (UA) for the point of interest.

23. The method of claim 21, wherein determining the at least one material property at the point of interest of the bone comprises determining at least one of elasticity, density, shear strength and tensile strength.

24. The method of claim 21, wherein timing signals are provided to a stepper motor for positioning the confocal point to a series of points of interest for detecting the region of interest in the bone.

25. The method of claim 20, wherein steps a-g are repeated for an array of points of interest in the bone, the array comprising a volume.

26. The method of claim 25, wherein points in the array are separated by 0.1 mm.

27. A system for determining at least one material property of a material sample at least one point, the system comprising:
 a) a transmitting ultrasonic transducer and a receiving ultrasonic transducer, both transducers being confocal transducers, the transducers configured to receive the material sample therebetween such that the confocal point of the transducers are located at the at least one point in the material sample; and
 b) a processor configured to initiate an ultrasonic signal from the transmitting transducers that is transmitted through the at least one point of the material sample when positioned between the transducers and received by the receiving transducer, the processor receiving a signal reflecting one or more measures of the received ultrasonic signal, the processor determining at least one ultrasonic parameter for the at least one point of the material sample based upon the transmitted and received ultrasonic confocal signals, the processor further determining the at least one material property at the point of the sample based upon the at least one ultrasonic parameter.

* * * * *